US006956111B2

(12) United States Patent
Danenberg

(10) Patent No.: US 6,956,111 B2
(45) Date of Patent: Oct. 18, 2005

(54) METHOD OF DETERMINING DIHYDROPYRIMIDINE DEHYDROGENASE GENE EXPRESSION

(75) Inventor: Kathleen D. Danenberg, Altadena, CA (US)

(73) Assignee: Response Genetics, Inc., New York, NY (US)

(*) Notice: Subject to any disclaimer, the term of this patent is extended or adjusted under 35 U.S.C. 154(b) by 0 days.

(21) Appl. No.: 09/796,807

(22) Filed: Mar. 2, 2001

(65) Prior Publication Data

US 2002/0123620 A1 Sep. 5, 2002

(51) Int. Cl.⁷ .......................... C07H 21/02; C12Q 1/68; C12P 19/34

(52) U.S. Cl. .................. 536/23.1; 536/24.3; 536/24.31; 536/24.33; 435/6; 435/91.2

(58) Field of Search .............................. 536/23.1, 24.3, 536/24.31, 24.33; 435/6

(56) References Cited

U.S. PATENT DOCUMENTS

| | | | |
|---|---|---|---|
| 4,830,969 A | 5/1989 | Holmes | 435/259 |
| 4,843,155 A | 6/1989 | Chomczynski | 536/27 |
| 5,128,247 A | 7/1992 | Koller | 435/91 |
| 5,284,940 A | 2/1994 | Lin et al. | 536/25.4 |
| 5,346,994 A | 9/1994 | Chomczynski | 530/419 |
| 5,502,166 A | 3/1996 | Mishina | 530/350 |
| 5,620,852 A | 4/1997 | Lin et al. | 435/6 |
| 5,637,687 A | 6/1997 | Wiggins | 536/25.4 |
| 5,643,767 A | 7/1997 | Fischetti et al. | 435/91.3 |
| 5,654,179 A | 8/1997 | Lin | 435/91.2 |
| 5,672,696 A | 9/1997 | Wang et al. | 536/25.42 |
| 5,707,802 A | 1/1998 | Sandhu et al. | 435/6 |
| 5,728,822 A | 3/1998 | Macfarlane | 536/25.41 |
| 5,736,531 A | 4/1998 | Von Borstel et al. | 514/50 |
| 5,777,099 A | 7/1998 | Mehra | 536/25.42 |
| 5,856,454 A | 1/1999 | Gonzalez et al. | 536/23.1 |
| 5,945,515 A | 8/1999 | Chomczynski | 530/412 |
| 5,989,857 A | 11/1999 | Mundschenk | 435/69.1 |
| 6,010,870 A | 1/2000 | Richt | 424/186.1 |
| 6,015,673 A | 1/2000 | Gonzalez et al. | 435/6 |
| 6,043,354 A | 3/2000 | Hillebrand et al. | 536/25.42 |
| 6,204,375 B1 | 3/2001 | Lader | 536/25.4 |
| 6,207,408 B1 | 3/2001 | Essenfeld et al. | 435/40.5 |
| 6,232,448 B1 * | 5/2001 | Yoshikuba | 530/388.26 |
| 6,248,535 B1 | 6/2001 | Danenberg et al. | 435/6 |

FOREIGN PATENT DOCUMENTS

| | | |
|---|---|---|
| DE | 198 37 391 A1 | 2/1999 |
| WO | WO 95/28489 A | 10/1995 |
| WO | WO 96/08568 | 3/1996 |
| WO | WO 97/05248 | 2/1997 |
| WO | WO 97/35034 | 9/1997 |
| WO | WO 98/41648 | 9/1998 |
| WO | WO 02/44423 A2 | 6/2002 |

OTHER PUBLICATIONS

Buck et al, "Design strategies and performance of custom DNA sequencing primers", Biotechniques (1999) 27(3):528–536.*

Peng et al, "Multiple PCR analyses on trace amounts of DNA extracted from fresh and paraffin wax embedded tissues after random hexamer primer PCR amplification", J. Clin. Pathol. 47(7):605–8.*

Promega Catalog 1992, p. 166.*

Iqbal, S. Lenz HJ, "Determinants of prognosis and response to therapy in colorectal cancer,"Curr Oncol Rep. Mar. 2001;3(2):102–8.

Gilmore PM, et al., "The Development and Optimisation of a Quantitative RT–PCR Technique from Formalin–Fixed and Paraffin–Embedded (FFPE) Tissues, Using the Thymidylate Synthase (TS) Gene As a Target," American Society of Clinical Oncology: 17: Abstract 2159, 1998.

Fujiwaki R, Hata K, Nakayama K, Fukumoto M, Miyazaki K, "Gene expression for dihydropyrimidine dehydrogenase and thymidine phosphorylase influences outcome in epithelial ovarian cancer," J Clin Oncol. Dec. 1, 2000;18(23):3946–51.

Takabayashi A, Iwata, S. Kawai Y, Kanai TM, Taki Y, Takechi T, Fukushima M., "Dihydropyrimidine dehydrogenase activity and mRNA expression in advanced gastric cancer analyzed in relation to effectiveness of preoperative 5–fluorouracil–based chemotherapy," Int J Oncol. Nov. 2000;17(5):889–95.

Salonga D, Danenberg KD, Johnson M, Metzger R, Groshen S, Tsao–Wei DD, Lerz HJ, Leichman CG, Leichman L, Diasio RB, Danenberg PV, "Colorectal tumors responding to 5–fluorouracil have low gene expression levels of dihydropyrimidine dehydroganase, thymidylate synthase, and thymidine phosphorylase," Clin Cancer Res. Apr. 2000;6(4):1322–7.

Nishiyama M, Yamamoto W, Park JS, Okamoto R, Hanaoka H, Takano H, Saito N, Matsukawa M, Shirasaka T, Kurihara M, "Low–dose cisplatin and 5–fluorouracil in combination can repress increased gene expression of cellular resistance determinants to themselves," Clin Cancer Res. Sep. 1999;5(9):2620–8.

(Continued)

Primary Examiner—Jeffrey Fredman
(74) Attorney, Agent, or Firm—Kenyon & Kenyon

(57) ABSTRACT

The present invention relates to prognostic methods which are useful in medicine, particularly cancer chemotherapy. The object of the invention to provide a method for assessing Dihydropyrimidine dehydrogenase (DPD) expression levels in tissues and prognosticate the probable resistance of a patient's tumor to treatment with 5-FU based therapies by examination of the amount of DPD mRNA in a patient's tumor cells and comparing it to a predetermined threshold expression level. More specifically, the invention provides to oligonucleotide primer pairs DPD3A and DPD3B and methods comprising their use for detecting levels of Dihydropyrimidine dehydrogenase (DPD) mRNA.

6 Claims, 2 Drawing Sheets

OTHER PUBLICATIONS

Kirihara Y. Yamamoto W. Toge T, Nishiyama M, "Dihydropyrimidine dehydrogenase, multidrug resistance–associated protein, and thymidylate synthase gene expression levels can predict 5–fluorouracil resistance in human gastrointestinal cancer cells," Int J Oncol. Mar. 1999;14(3):551–6.

Nita ME, Tominaga O, Nagawa H, Tsuruo T, Muto T, "Dihydropyrimidine dehydrogenase but not thymidylate synthase expression is associated with resistance to 5–fluorouracil in colorectal cancer," *Hepatogastroenterology*, Nov.–Dec. 1998;45(24):2117–22.

Ishikawa et al., "Dehydrogenase activity and messenger RNA level may be related to the antitumor effects of 5–FU on human tumor xenografts in nude mice," Clin. Cancer Res., 5: 883–889, 1999.

Johnson et al, "Quantitation of dihydropyrimidine dehydrogenase expression by real–time reverse transcription polymerase chain reaction," Analyt. Biochem. 278: 175–184, 2000.

Shirota Y, Ichikawa W, Yamada H, Uetake H, Nihei Z, Sugihara K, "Dihydropyrimidine dehydrogenase gene expression in patients with hepatic metastases from colorectal cancer," Gan To Kagaku Ryoho Oct. 1999; 26(12):1729–31.

Specht K, Richter T, Muller U, Walch A, Werner M, Hofler H, "Quantitative gene expression analysis in microdissected archival formalin–fixed and paraffin–embedded tumor tissue," Am J Pathol. Feb. 2001;158(2):419–2.

Gibson, UE, "A novel method for real timequantitative RT–PCR,"Genome Res. 6: 995–1001, 1996.

Heid, CA, Real Time quantitative PCR, Genome Res. 6: 986–994, 1996.

Leichman et al., Quantitation of intratumoral thymidylate synthase expression predicts for disseminated colorectal cancer response and resistance to protracted–infusion fluorouracil and weekly leucovorin. J Clin Oncol. Oct. 1997; 15(10):3223–9.

Harris et al., Relationship between dihydropyrimidine dehydrogenase activity and plasma 5–fluorouracil levels with evidence for circadian variation of enzyme activity and plasma drug levels in cancer patients receiving 5–fluorouracil by protracted continuous infusion. Cancer Res. Jan. 1, 1990;50(1):197–201.

Etienne et al., Response to fluorouracil therapy in cancer patients: the role of tumoral dihydropyrimidine dehydrogenase activity. J Clin Oncol. 1995 Jul.;13(7):1663–70.

Beck et al., A role for dihydropyrimidine dehydrogenase and thymidylate synthase in tumour sensitivity to fluorouracil. Eur J Cancer. 1994; 30A(10):1517–224.

Johnston et al., TS Expression from Formalin Fixed Paraffin Embedded (FFPE) tissues using Quantitative RT–PCR correlates with frozen tissue data and predicts for response to 5–FU in metastatic colorectal cancers. American Society of Clinical Oncology: Astract 2383, 1999.

Ichikawa et al., Expression of DPD in primary lesion predicts the anti–tumor effect in 5–FU based Chemotherapy gor GI tract cancer. American Society of Clinical Oncology: Astract 1114, 2000.

Danenberg etl., DPD and TS expressions identify a high percentage of colorectal tumors responding to 5–FU. American Society of Clinical Oncology: Astract 992, 1998.

Nihei, Z., Expression of Dihydropyrimidine Dehydrogenase (DPD) in Gastric Cancer, 36th Annual Meeting of the American Scoeity of Clinical Oncology, Gastric Cancer, 1176, May 20–23, 2000.

Ishikawa Y, Kubota T, Otani, Y, Watanabe M, Teramoto T, Kumai K, Takechi T, Okabe H, Fukushima M, Kitajima M., Dihydropyrimidine dehydrogenase and messenger RNA levels in gastric cancer: possible predictor for sensitivity to 5–fluorouracil.Jpn J Cancer Res. Jan. 2000;91(10):105–12.

Ishikawa Y, Kubota T, Otani Y, Watanabe M, Teramoto T, Kumai K, Takechi T, Okabe H, Fukushima M, Kitajima M., Thymidylate synthetase and dihydropyrimidine dehydrogenase levels in gastric cancer. Anticancer Res. Nov.–Dec. 1999;19(6C):5635–40.

Scherf U, Ross DT, Waltham M, Smith LH, Lee JK, Tanabe L, Kohn KW, Reinhold WC, Myers TG, Andrews DT, Scudiero DA, Eisen MD, Sausville EA, Pommier Y, Botstein D, Brown PO, Weinstein JN. A gene expression database for the molecular pharmacology of cancer.Nat Genet. Mar. 2000;24(3):236–44.

Huang CL, Yokomise H, Kobayashi S, Fukushima M, Hitomi S, Wada H. Intratumoral expression of thmidylate synthase and dihydropyrimidine dehydrogenase in non–small cell lung cancer patients treated with 5–FU–based chemotherpay. Int J Oncol. 2000 Jul.17(1):47–54.

Takechi T, Okabe H, Fujioka A, Murakami Y, Fukushima M. Relationship between protein levels and gene expression of dihydropyrimidine dehydrogenase in human tumor cells during growth in culture and in nude mice. Jpn J Cancer Res. Nov. 1998;89(11):1144–53.

Uetake H, Ichikawa W, Takechi T, Fukushima M, Mihei Z, Sugihara K. Relationship between intratumoral dihydropyrimidine dehydrogenase activity and gene expression in human colorectal cancer. Clin Cancer Res. Oct. 1999;5(10):2836–9.

Ichikawa, et al, "Expression of Dihydropyrimidine Dehydrogenase (DPD) and Thymidylate Synthase (TS) mRNA in Primary Tumor Predicts the Anti–Tumor Effect in 5–Fluorouracil (FU Based Chemotherapy for Gastrointestinal (GI Cancer", American Association for Cancer Research, Proceedings of the American Association for Cancer Research, 92nd Annual Meeting, vol. 42, Mar. 2001. Abstract No. 3326.

G. Stanta, et al., *RNA Quantitative Analysis from Fixed and Paraffin–Embedded Tissues*, Methods in Molecular Biology (1998) vol. 86, pp. 113–119.

G. Stanta, et al., *RNA Extraction from Formalin–Fixed and Paraffin–Embedded Tissues*, Methods in Molecular Biology (1998) vol. 86, pp. 23–26.

I. Miyauchi, et al., "Further study of hepatitis C virus RNA detection in formalin –fixed, paraffin –embedded liver tissues b ligation –dependent polymerase chain reaction" Pathology International 1998:48: 428–432.

J. Grem et al., "Thymidine kinase, thymidylate synthase, and dihydropyrimidine dehydrogenase profiles of cell lines of the National Cancer Institute's anticancer drug screen" Clinical Cancer Research, vol. 7, 999–1009, Apr. 2001.

Willhauck et al., "Internal Control for Quality Assurance of Diagnostic RT–PCR", BioTechniques 25: Oct. 1998; pp. 656–659.

Ardalan, B., et al., "*Thymidylate Synthase Gene Expression in Normal and Malignant Colorectal Tissues: Relation to in vivo Response and Survival,*" Proceedings of the American Association for Cancer Research, vol. 37, Abstract No. 1376 (Mar. 1996).

Ausubel, F.M., ed., *Current Protocols In Molecular Biology*, John Wiley & Sons, Inc., vol. 1.; Strauss, W.M., "Preparation of Genomic DNA from Mammalian Tissue," Unit 2.2 pp. 2.2.1–2.2.3 (1998).

Ausubel, F.M., ed., *Current Protocols In Molecular Biology*, John Wiley & Sons, Inc., vol. 1.; Richards, E., et al., "Preparation of Genomic DNA from Plant Tissue," Unit 2.3, pp. 2.3.1–2.3.7 (1994).

Ausubel, F.M., ed., *Current Protocols In Molecular Biology*, John Wiley & Sons, Inc., vol. 1.; Wilson, K., "Preparation of Genomic DNA from Bacteria," Unit 2.4, pp. 2.4.1–2.4.5 (1994).

Banerjee, S.K., et al, "Microwave–Based DNA Extraction from Paraffin–Embedded Tissue for PCR Amplification," BioTechniques, vol. 18, No. 5, pp. 768, 770, 772, 773 (1995).

Benhattar, J., et al., "p53 Mutations as a Possible Predictor of Response to Chemotherapy in Metastatic Colorectal Carcinomas," Int. J. Cancer (Pred. Oncol.), vol. 69, pp. 190–192 (1996).

Bresters, D., et al., "Detection of Hepatitis C Viral RNA Sequences in Fresh and Paraffin–Embedded Liver Biopsy Specimens of Non–A, Non–B Hepatitis Patients," J. Hepat., vol. 15, pp. 391–395 (1992).

Bresters, D., et al., "The Duration of Fixation Influences the Yield of HCV cDNA–PCR Products from Formalin–Fixed, Paraffin–Embedded Liver Tissue," J. Virol. Method, vol. 48, pp. 267–272 (1994).

Chirgwin, J., M., et al., "Isolation of Biologically Active Ribonucleic Acid from Sources Enriched in Ribonuclease," Biochemistry, vol. 18, No. 24, pp. 5294–5299 (1979).

Chomczynski, P., et al., "Single–Step Method of RNA Isolation by Acid Guanidinium Thiocyanate–Phenol–Chloroform Extraction," Analytical Biochemistry, vol. 162, pp. 156–159 (1987).

Chomczynski, P., "A Reagent for the Single–Step Simultaneous Isolation of RNA, DNA and Proteins from Cell and Tissue Samples," BioTechniques, vol. 15, No. 3, pp. 532–534, 536–537 (1993).

Coombs, N. J., et al., "Opimisation of DNA and RNA Extraction from Archival Formalin–Fixed Tissue," Nucl. Acids Research, vol. 27, No. 16, pp. i–iii (1999).

Dakhama, A., et al., "Amplification of Human β–Actin Gene by the Reverse Transcripase–Polymerase Chain Reaction: Implications for Assessment of RNA from Formalin–Fixed, Paraffin–Embedded Material," J. Histochem. and Cytochem., vol. 44, No. 10, pp. 1205–1207 (1996).

de Andrés, B., et al., "Improved Method for mRNA Extraction from Paraffin–Embedded Tissues," BioTechniques, vol. 18, No. 1, pp. 42–43 (1995).

Eads, C. A., et al., "CpG Island Hypermethylation in Human Colorectal Tumors is Not Associated with DNA Methyltransferase Overexpression," Cancer Research, vol. 59, pp. 2302–2306 (1999).

Edamoto, Y., et al., "Hepatitis C and B Virus Infections in Hepatocellular Carcinoma," Cancer, vol. 77, No. 9, pp. 1787–1791 (1996).

Farrugia, D., et al., "A pharmacodynamic (PD) study of the thymidylate, synthase (TS) Inhibitor Tomudex™ in advanced colorectal cancer (CRC)," Proceedings of the American Association for Cancer Research, Eighty–eighth Annual Meeting (Apr. 12–16, 1997), vol. 38 (1997), Abstract #4132.

Finke, J., et al., "An Improved Strategy and a Useful Housekeeping Gene for RNA Analysis from Formalin–Fixed, Paraffin–Embedded Tissues by PCR," BioTechniques, vol. 14, No. 3, pp. 448–53 (1993).

Goldsworthy, S. M., et al., "Effects of Fixation on RNA Extraction and Amplification from Laser Capture Microdissected Tissue," Molecular Carcinogenesis, vol. 25, pp. 86–91 (1999).

Greer, C. E., et al., "PCR Amplification from Paraffin–Embedded Tissues," Am. J. Clin. Pathol., vol. No. 95, No. 2, pp. 117–24 (1991).

Gruber, A. D., et al., "Detection of Bovine Viral Diarrhea Virus RNA in Formalin–Fixed, Paraffin–Embedded Brain Tissue by Nested Polymerase Chain Reaction," J. Virol. Methods, vol. 43, pp. 309–319 (1993).

Guerrero, R.B., et al., "Effects of Formalin Fixation and Prolonged Block Storage on Detection of Hepatitis C Virus RNA in Liver Tissue," Diag. Molec. Path., vol. 6, No. 5, pp. 277–281 (1997).

Hodges, E., et al., "Isolation of Nucleic Acid from Paraffin Embedded Tissue for PCR Amplification and Sequencing of TcR Vβ Genes," Leuk. Research, vol. 19, No. 3, pp. 183–186 (1995).

Horie, N., et al., "Functional Analysis and DNA Polymorphism of the Tandemly Repeated Sequences in the 5' terminal Regulatory Region of the Human Gene for Thymidylate Synthase," Cell Structure and Function, vol. 20, No. 3, pp. 191–197 (1995).

Horikoshi, T., et al, "Quantitation of Thymidylate Synthase, Dihydrofolate Reductase, and DT–Diaphorase Gene Expression in Human Tumors using the Polymerase Chain Reaction," Cancer Res., vol. 52, pp. 108–116 (1992).

Hsuih, T. C. H., et al., "Novel, Ligation–Dependent PCR Assay for Detection of Hepatitis C Virus in Serum," J. Clin. Microbiol., vol. 34, No. 3, pp. 501–507 (1996).

Iwamoto, K. S., et al., "Feasibility of Using Decades–Old Archival Tissues in Molecular Oncology/Epidmiology," Am. J. Path., vol. 149, No. 2, pp. 399–406 (1996).

Jackman, A. L., et al., "Thymidylate Synthetase Inhibitors: Experimental and Clinical Aspects," Chapter 7 in Experimental and Clinical Progress in Cancer Chemotherapy, F.M. Muggia, ed., Martinus Nijhoff, Boston (1985), pp. 155–210.

Jiang, Y.–H., et al., "A Rapid RT–PCR Method for Detection of Intact RNA in Formalin–Fixed Paraffin–Embedded Tissues," Nucl. Acids. Res., vol. 23, No. 15, pp. 3071–3072 (1995).

Kawakami, K., et al., "Polymorphic Tandem Repeats in the Thymidylate Synthase Gene is Associated with its Protein Expression in Human Gastrointestinal Cancers," Proceedings of the American Society of Clinical Oncology, vol. 17, Abstract No. 1128 (May 1998).

Keyomarsi, K., et al., "Mechanism of the Cytotoxic Synergism of Fluoropyrimidines and Folinic Acid in Mouse Leukemic Cells," J. Biol. Chem., vol. 263, No. 28, pp. 14402–14409 (1988).

Kiyosawa, K., et al., "Interrelationship of Blood Transfusion, Non–A, Non–B Hepatitis and Hepatocellular Carcinoma: Analysis by Detection of Antibody to Hepatitis C Virus," Hepatology, vol. 12, No. 4, pp. 671–675 (1990).

Koopmans, M., et al., "Optimization of Extraction and PCR Amplification of RNA Extracts from Paraffin–Embedded Tissue in Different Fixatives," J. Virological Methods, vol. 43, pp. 189–204 (1993).

Lenz, H.-J., et al., "*p53 and Thymidylate Synthase Expression in Untreated Stage II Colon Cancer: Associations with Recurrence, Survival, and Site,*" Clinical Cancer Research, vol. 4, pp. 1227–1234 (1998).

Lenz, H.-J., et al., "*Thymidylate Synthase mRNA Level in Adenocarcinoma of the Stomach: A Predictor for Primary Tumor Response and Overall Survival,*" J. Clinical Oncology, vol. 14, No. 1, pp. 176–182 (1996).

Macfarlane, D. E., et al., "*Introduction to Isolating RNA,*" in RNA Isolation and Characterization Protocols, R. Rapley and D. L. Manning, eds., Humana Press (Series: Methods in Molecular Biology™), Totowa, N. J. (1998), pp. 1–6.

Marsh, S., et al., "*Ethnic Variation in the Thymidylate Synthase Enhancer Region Polymorphism among Caucasian and Asian Populations,*" Genomics, vol. 58, pp. 310–312 (1999).

Mies, C., "*A Simple, Rapid Method for Isolating RNA from Paraffin–embedded Tissues for Reverse Transcription–Polymerase Chain Reaction (RT–PCR),*" J. Histochemistry and Cytochemistry, vol. 42, No. 6, pp. 811–813 (1994).

Miyauchi I., et al., "*Further study of hepatitis C virus RNA detection in formalin–fixed, paraffin–embedded liver tissues by ligation–dependent polymerase chain reaction*", Pathology International, vol. 48, pp. 428–432 (1998).

Mizuno, T., et al., "*RNA from Decades–Old Archival Tissue Blocks for Retrospective Studies,*" Diagnostic Molecular Pathology, vol. 7, No. 4, pp. 202–208 (1998).

Mukhopadhyay, T., et al., "*Isolation of Total RNA from Tissues or Cell Lines,*" in RNA Isolation and Characterization Protocols, R. Rapley and D. L. Manning, eds., Humana Press (Series: Methods in Molecular Biology™), Totowa, N.J. (1998), pp. 55–59.

Park, Y. N., et al., "*Detection of Hepatitis C Virus RNA Using Ligation–Dependent Polymerase Chain Reaction in Formalin–Fixed, Paraffin–Embedded Liver Tissues,*" American Journal of Pathology, vol. 149, No. 5, pp. 1485–1491 (1996).

Rupp, G. M., et al., "*Purification and Analysis of RNA from Paraffin–Embedded Tissues,*" BioTechniques, vol. 6, No. 1, pp. 56–60 (1988).

Sambrook, J., et al., "*Isolation of High–Molecular Weight DNA from Mammalian Cells,*" in Molecular Cloning: A Laboratory Manual, $2^{nd}$ Ed., Cold Spring Harbor Laboratory Press (1989), pp. 9.14–9.23.

Sander, C. A., et al., "*p53 Mutation is Associated with Progression in Follicular Lymphomas,*" Blood, vol. 82, No. 7, pp. 1994–2004 (1993).

Santos, A. C., et al., "*Simultaneous Extraction of RNA and DNA from Paraffin–Embedded Tissues,*" Trends in Genetics, vol. 9, No. 7, p. 231 (1993).

Soguero, C., et al., "*Detection of Hepatitis C Virus RNA in More Than 20–Year Old Paraffin–Embedded Liver Tissue,*" Laboratory Investigation, vol. 79, No. 3, pp. 365–366 (1999).

Sorg, I., et al., "*Detection of Borna Disease Virus RNA in Formalin–Fixed, Paraffin–Embedded Brain Tissues by Nested PCR,*" J. Clinical Microbiology, vol. 33, No. 4, pp. 821–823 (1995).

Spears, C. P., et al., "*In Vivo Kinetics of Thymidylate Synthetase Inhibition in 5–Fluorouracil–Sensitive and – Resistant Murine Colon Adenocarcinomas,*" Cancer Research, vol. 42, pp. 450–456 (1982).

Stanta, G., et al., "*RNA Extracted from Paraffin–Embedded Human Tissues is Amenable to Analysis by PCR Amplification,*" BioTechniques, vol. 11, No. 3, pp. 304–308 (3 pages) (1991).

Swain, S. M., et al., "*Fluorouracil and High–Dose Leucovorin in Previously Treated Patients with Metastatic Breast Cancer,*" J. Clinical Oncology, vol. 7, No. 7, pp. 890–899 (1989).

Wei, X., et al., "*Molecular Basis of the Human Dihydropyrimidine Dehydrogenase Deficiency and 5–Fluorouracil Toxicity,*" J. Clinical Investigation, vol. 98, No. 3, pp. 610–615 (1996).

v. Weizsäcker, F., et al., "*A Simple and Rapid Method for the Detection of RNA in Formalin–Fixed, Paraffin–Embedded Tissues by PCR Amplification,*" Biochem. and Biophys. Research Comm., vol. 174, No. 1, pp. 176–180 (1991).

\* cited by examiner

Fig. 1. Comparison of 4 DPD primer/probe sets for their ability to amplify DPD mRNA.
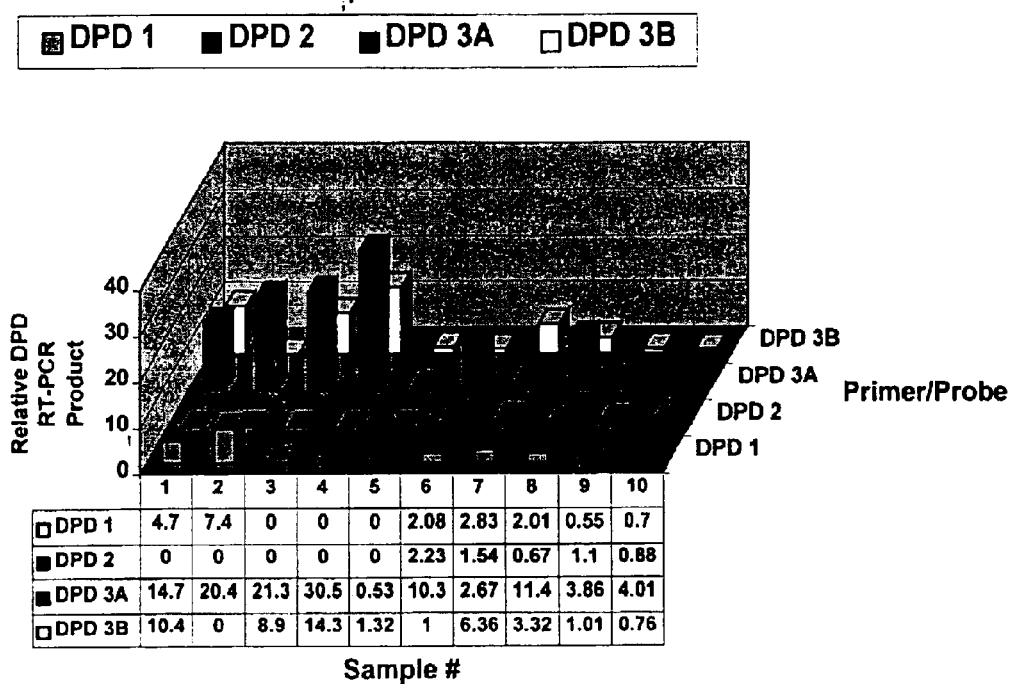

Fig. 2. Comparison of amplification efficiency of primer/probe DPD 3A and DPD 1 to amplify DPD mRNA from frozen tissue.
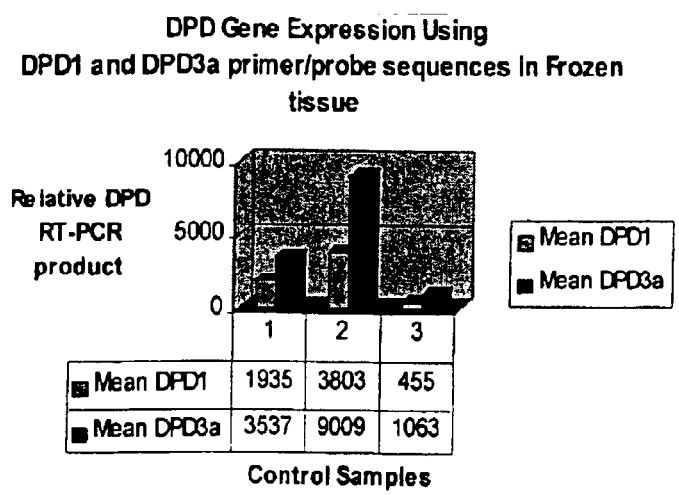

METHOD OF DETERMINING DIHYDROPYRIMIDINE DEHYDROGENASE GENE EXPRESSION

FIELD OF THE INVENTION

The present invention relates to prognostic methods which are useful in medicine, particularly cancer chemotherapy. The invention also relates to assessment of gene expression of tumor cells of a patient. More specifically, the invention relates to oligonucleotides and methods comprising their use for detecting levels of Dihydropyrimidine dehydrogenase (DPD) mRNA expression using RT-PCR.

BACKGROUND OF THE INVENTION

Cancer arises when a normal cell undergoes neoplastic transformation and becomes a malignant cell. Transformed (malignant) cells escape normal physiologic controls specifying cell phenotype and restraining cell proliferation. Transformed cells in an individual's body thus proliferate in the absence of these normal controls, thus forming a tumor. When a tumor is found, the clinical objective is to destroy malignant cells selectively while mitigating any harm caused to normal cells in the individual undergoing treatment.

Chemotherapy is based on the use of drugs that are selectively toxic (cytotoxic) to cancer cells. Several general classes of chemotherapeutic drugs have been developed, including drugs that interfere with nucleic acid synthesis, protein synthesis, and other vital metabolic processes.

5-Fluorouracil (5-FU) is a very widely used drug used for the treatment of many different types of cancers, including major cancers such as those of the GI tract and breast (Moertel, C. G. New Engl. J. Med., 330:1136–1142, 1994). 5-FU as a single agent was for more than 40 years the standard first-line treatment for colorectal cancer, but it was supplanted as "standard of care" by the combination of 5-FU and CPT-11 (Saltz et al., Irinotecan Study Group. New England Journal of Medicine. 343:905–14, 2000). Recently, the combination of 5-FU and oxaliplatin has produced high response rates in colorectal cancers (Raymond et al., Semin. Oncol., 25:4–12, 1998). Thus, it is likely that 5-FU will be used in cancer treatment for many years because it remains the central component of current chemotherapeutic regimens. In addition, single agent 5-FU therapy continues to be used for patients in whom combination therapy with CPT-11 or oxaliplatin is likely to be excessively toxic.

5-FU is typical of most anti-cancer drugs in that only the minority of patients experience a favorable response to the therapy. Large randomized clinical trials have shown the overall response rates of tumors to 5-FU as a single agent for patients with metastatic colorectal cancer to be in the 15–20% range (Moertel, C. G. New Engl. J. Med., 330:1136–1142, 1994). In combination with other chemotherapeutics mentioned above, tumor response rates to 5-FU-based regimens have been increased to almost 40%. Nevertheless, the majority of treated patients derive no tangible benefit from having received 5-FU based chemotherapy, and are subjected to significant risk, discomfort, and expense. Since there has been no reliable means of anticipating the responsiveness of an individual's tumor prior to treatment, the standard clinical practice has been to subject all patients to 5-FU-based treatments, fully recognizing that the majority will suffer an unsatisfactory outcome.

The mechanism of action and the metabolic pathway of 5-FU have been intensively studied over the years to identify the most important biochemical determinants of the drug's anti-tumor activity. The ultimate goal was to improve the clinical efficacy of 5-FU by a) modulation of its intracellular metabolism and biochemistry and b) by measuring response determinants in patients' tumors prior to therapy to predict which patients are most likely to respond (or not to respond) to the drug. Two major determinants emerged from these studies: 1) the target enzyme of 5-FU, thymidylate synthase (TS) and 2) the catabolic enzyme dihydropyrimidine dehydrogenase (DPD).

The first studies in the area of tumor response prediction to 5-FU based therapy centered on the target enzyme TS in colorectal cancer. Leichman et al (Leichman et al., J. Clin Oncol., 15:3223–3229, 1997) carried out a prospective clinical trial to correlate tumor response to 5-FU with TS gene expression as determined by RT-PCR in pre-treatment biopsies from colorectal cancers. This study showed: 1) a large 50-fold range of TS gene expression levels among these tumors, and 2) strikingly different levels of TS gene expression between responding and non-responding tumors. The range of TS levels of the responding groups (0.5–4.1, relative to an internal control) was narrower than that of the non-responding groups (1.6–23.0, relative to an internal control). The investigators determined a resulting "non-response cutoff" threshold level of TS expression above which there were only non-responders. Thus, patients with TS expression above this "non-response cutoff" threshold could be positively identified as non-responders prior to therapy. The "no response" classification included all therapeutic responses with <50% tumor shrinkage, progressing growth resulting in a >25% tumor increase and non-progressing tumors with either <50% shrinkage, no change or <25% increase. These tumors had the highest TS levels. Thus, high TS expression identifies especially resistant tumors. TS expression levels above a certain threshold identified a subset of tumors not responding to 5-FU, whereas TS expression levels below this number predicted an appreciably higher response rate yet did not specifically identify responding tumors.

Subsequent studies investigated the usefulness of DPD expression levels as a tumor response determinant to 5-FU treatment in conjunction with TS expression levels. DPD is a catabolic enzyme which reduces the 5,6 double bond of 5-FU, rendering it inactive as a cytotoxic agent. Previous studies have shown that DPD levels in normal tissues could influence the bio-availability of 5-FU, thereby modulating its pharmacokinetics and anti-tumor activity (Harris et al., Cancer Res., 50: 197–201, 1990). Additionally, evidence has been presented that DPD levels in tumors are associated with sensitivity to 5-FU (Etienne et al., J. Clin. Oncol., 13: 1663–1670, 1995; Beck et al., Eur. J. Cancer, 30: 1517–1522, 1994). Salonga et al, (Clin Cancer Res., 6:1322–1327, 2000) investigated gene expression of DPD as a tumor response determinant for 5-FU/leucovorin treatment in a set of tumors in which TS expression had already been determined. As with TS, the range of DPD expression among the responding tumors was relatively narrow (0.6–2.5, 4.2-fold; relative to an internal control) compared with that of the non-responding tumors (0.2–16, 80-fold; relative to an internal control). There were no responding tumors with a DPD expression greater than a threshold level of about 2.5. Furthermore, DPD and TS expression levels showed no correlation with one another, indicating that they are independently regulated genes. Among the group of tumors having both TS and DPD expression levels below their respective "non-response cut-off" threshold levels, 92% responded to 5-FU/LV. Thus, responding tumors could be identified on the basis of low expression levels of DPD and TS.

DPD is also an important marker for 5-FU toxicity. It was observed that patients with very low DPD levels (such as in DPD Deficiency Syndrome; i.e. thymine uraciluria) undergoing 5-FU based therapy suffered from life-threatening toxicity (Lyss et al., Cancer Invest., 11: 2390240, 1993). Indeed, the importance of DPD levels in 5-FU therapy was dramatically illustrated by the occurrence of 19 deaths in Japan from an unfavorable drug interaction between 5-FU and an anti-viral compound Sorivudine (Diasio et al., Br. J. Clin. Pharmacol. 46, 1–4, 1998) It was subsequently discovered that a metabolite of Sorivudine is a potent inhibitor of DPD. This treatment resulted in DPD Deficiency Syndrome-like depressed levels of DPD which increased the toxicity of 5-FU to the patients (Diasio et al., Br. J. Clin. Pharmacol. 46, 1–4, 1998).

Thus, because of a) the widespread use of 5-FU protocols in cancer treatment, b) the important role of DPD expression in predicting tumor response to 5-FU and c) the sensitivity of individuals with DPD-Deficiency Syndrome to common 5-FU based treatments, it is clear that accurate determination of DPD expression levels prior to chemotherapy will provide an important benefit to cancer patients.

Measuring DPD enzyme activity requires a significant amount of fresh tissue that contains active enzyme. Unfortunately, most pre-treatment tumor biopsies are available only as fixed paraffin embedded (FPE) tissues, particularly formalin-fixed parafin embedded tissues which do not contain active enzyme. Moreover, biopsies generally contain only a very small amount of heterogeneous tissue.

RT-PCR primer and probe sequences are available to analyze DPD expression in frozen tissue or fresh tissue. However, those primers are unsuitable for the quantification of DPD mRNA from fixed tissue by RT-PCR. Heretofore, existing primers give no or erratic results. This is thought to be due to the a) inherently low levels of DPD RNA; b) very small amount of tissue embedded in the paraffin; and c) degradation of RNA in the paraffin into short pieces of <100 bp. As a result, other investigators have made a concerted yet unsuccessful efforts to obtain oligonucleotide primer sets allowing for such a quantification of DPD expression in paraffinized tissue. Thus, there is a need for method of quantifying DPD mRNA from fixed tissue in order to provide an early prognosis for proposed cancer therapies. Because it has been shown that DPD enzyme activity and corresponding mRNA expression levels are well correlated (Ishikawa et al., Clin. Cancer Res., 5:883–889, 1999; Johnson et al., Analyt. Biochem. 278: 175–184, 2000), measuring DPD mRNA expression in FPE specimens provides a way to assess the DPD expression levels status of patients without having to determine enzyme activity in fresh tissues. Furthermore, FPE specimens are readily amenable to microdissection, so that DPD gene expression can be determined in tumor tissue uncontaminated with stromal tissue.

Accordingly, it is the object of the invention to provide a method for assessing DPD levels in tissues and prognosticate the probable resistance of a patient's tumor to treatment with 5-FU based therapies, by examination of the amount of DPD mRNA in a patient's tumor cells and comparing it to a predetermined threshold expression level.

SUMMARY OF THE INVENTION

In one aspect of the invention there is provided oligonucleotide primers having the sequence of DPD3A-51F (SEQ ID NO: 1) or DPD3A-134R (SEQ ID NO:2), as well as oligonucleotide primers DPD3b-651F (SEQ ID NO: 7) and DPD3b-736R (SEQ ID NO: 8) and sequences substantially identical thereto. The invention also provides for oligonucleotide primers having a sequence that hybridizes with DPD3A-51F (SEQ ID NO: 1), DPD3A-134R (SEQ ID NO: 2), DPD3b-651F (SEQ ID NO:7), DPD3b-736R (SEQ ID NO: 8) or complements thereof under stringent conditions.

Moreover, this invention relates to a method for determining a chemotherapeutic regimen, comprising obtaining an mRNA sample from a tumor specimen; determining DPD gene expression level in the specimen; comparing the determined DPD gene expression levels with a predetermined threshold level for that gene; and determining a chemotherapeutic regimen based on the results of the comparison of the determined gene expression level with the predetermined threshold level.

BRIEF DESCRIPTION OF THE DRAWINGS

FIG. 1 is a graph showing a comparison of four different oligonucleotide primer pairs for their ability to amplify DPD mRNA derived from 10 different formalin-FPE tissue samples. Samples #1–5, and #8–10 are derived from colon tumor, #6 from bronchoalveolar tumor and #7 from small bowel tumor biopsies. Oligonucleotide primer pairs DPD1 (DPD-70F, (SEQ ID NO: 3) and DPD-201R, (SEQ ID NO: 4)), DPD2 (DPD2p-1129F (SEQ ID NO: 5) and DPD2p-1208R (SEQ ID NO: 6)) are not effective in measuring DPD mRNA levels in these samples. Oligonucleotide primer pairs DPD3A (DPD3a-51F (SEQ ID NO: 1) and DPD3a-134R (SEQ ID NO: 2)) and DPD3B (DPD3b-651F (SEQ ID NO: 7) and DPD3b-736R (SEQ ID NO: 8)) are effective in ascertaining DPD levels in various samples.

FIG. 2 is a graph showing a comparison of DPD mRNA amplification efficiency of the oligonucleotide primer pairs DPD3A (DPD3a-51F (SEQ ID NO: 1) and DPD3a-134R (SEQ ID NO: 2)) and DPD1 (DPD-70F (SEQ ID NO: 3) and DPD-201R (SEQ ID NO: 4)) in frozen tissue samples. The graph illustrates that not only is the oligonucleotide primer pair DPD3A (DPD3a-51F (SEQ ID NO: 1) and DPD3a-134R (SEQ ID NO: 2)) also effective in measuring DPD expression levels in frozen tissue samples (as well as FPE derived samples) it is more efficient than the oligonucleotide primer pair DPD1 (DPD-70F (SEQ ID NO: 3) and DPD-201R (SEQ ID NO: 4)).

DETAILED DESCRIPTION OF THE INVENTION

The present inventors disclose oligonucleotide primers and oligonucleotide primers substantially identical thereto that allow accurate assessment of DPD expression in tissues. These oligonucleotide primers, DPD3 a-51F (SEQ ID NO: 1) and DPD3a-134R (SEQ ID NO: 2), (also referred to herein as the oligonucleotide primer pair DPD3A) and oligonucleotide primers DPD3b-651F (SEQ ID NO: 7) and DPD3b-736R (SEQ ID NO: 8), (also referred to herein as the oligonucleotide primer pair DPD3B) are particularly effective when used to measure DPD gene expression in fixed paraffin embedded (FPE) tumor specimens.

"Substantially identical" in the nucleic acid context as used herein, means that the oligonucleotides hybridizes to a target under stringent conditions, and also that the nucleic acid segments, or their complementary strands, when compared, are the same when properly aligned, with the appropriate nucleotide insertions and deletions, in at least about 60% of the nucleotides, typically, at least about 70%, more typically, at least about 80%, usually, at least about 90%, and more usually, at least, about 95–98% of the nucleotides. Selective hybridization exists when the hybridization is more selective than total lack of specificity. See, Kanehisa, Nucleic Acids Res., 12:203–213 (1984).

This invention includes substantially identical oligonucleotides that hybridize under stringent conditions (as defined herein) to all or a portion of the oligonucleotide primer sequence of DPD3A-51F (SEQ ID NO:1), its complement, DPD3A-134R (SEQ ID NO: 2) or its complement. Furthermore, this invention also includes substantially identical oligonucleotides that hybridize under stringent conditions (as defined herein) to all or portion of the oligonucleotide primer sequence DPD3b-651F (SEQ ID NO: 7) its complement, DPD3b-736R (SEQ ID NO: 8), or its complement.

Under stringent hybridization conditions, only highly complementary, i.e., substantially similar nucleic acid sequences hybridize. Preferably, such conditions prevent hybridization of nucleic acids having 4 or more mismatches out of 20 contiguous nucleotides, more preferably 2 or more mismatches out of 20 contiguous nucleotides, most preferably one or more mismatch out of 20 contiguous nucleotides.

The hybridizing portion of the nucleic acids is typically at least 10 (e.g., 15) nucleotides in length. The hybridizing portion of the hybridizing nucleic acid is at least about 80%, preferably at least about 95%, or most preferably about at least 98%, identical to the sequence of a portion or all of oligonucleotide primer DPD3A-51F (SEQ ID NO: 1), its complement, DPD3A-134R (SEQ ID NO: 2) or its complement. Additionally, the hybridizing portion of the hybridizing nucleic acid is at least least about 80%, preferably at least about 95%, or most preferably about at least 98%, identical to the sequence of a portion or all of oligonucleotide primer DPD3b-651F (SEQ ID NO: 7), its complement, DPD3b-736R (SEQ ID NO: 8) or its complement.

Hybridization of the oligonucleotide primer to a nucleic acid sample under stringent conditions is defined below. Nucleic acid duplex or hybrid stability is expressed as a melting temperature ($T_m$), which is the temperture at which the probe dissociates from the target DNA. This melting temperature is used to define the required stringency conditions. If sequences are to be identified that are substantially identical to the probe, rather than identical, then it is useful to first establish the lowest temperature at which only holmologous hybridization occurs with a particular concentration of salt (e.g. SSC or SSPE). Then assuming that 1% mismatching results in a 1° C. decrease in $T_m$, the temperatre of the final wash in the hybridization reaction is reduced accordingly (for example, if sequences having >95% identity with the probe are sought, the final wash temperature is decrease by 5° C.). In practice, the change in $T_m$ can be between 0.5° C. and 1.5° C. per 1% mismatch.

Stringent conditions involve hybridizing at 68° C. in 5×SSC/5×Denhart's solution/1.0% SDS, and washing in 0.2×SSC/0.1% SDS at room temperature. Moderately stringent conditions include washing in 3×SSC at 42° C. The parameters of salt concentration and temperature be varied to achieve optimal level of identity between the primer and the target nucleic acid. Additional guidance regarding such conditions is readily available in the art, for example, Sambrook, Fischer and Maniatis, Molecular Cloning, a laboratory manual, (2nd ed.), Cold Spring Harbor Laboratory Press, New York, (1989) and F. M. Ausubel et al eds., Current Protocols in Molecular Biology, John Wiley and Sons (1994).

This aspect of the invention involves use of a method for reliable extraction of RNA from an FPE specimen and second, determination of the content of DPD mRNA in the specimen by using oligonucleotide primers oligionucleotide primer pair DPD3A (DPD3a-51F (SEQ ID NO: 1) and DPD3a-134R (SEQ ID NO: 2)) or oligonucleotides substantially identical thereto or DPD3B (DPD3b-651F (SEQ ID NO: 7) and DPD3b-736R (SEQ ID NO: 8)) or oligonucleotides substantially identical thereto, for carrying out reverse transcriptase polymerase chain reaction. RNA is extracted from the FPE cells by any of the methods for mRNA isolation from such samples as described in U.S. patent application Ser. No. 09/469,338, filed Dec. 20, 1999, and is hereby incorporated by reference in its entirety.

The present invention resides in part in the finding that the relative amount of DPD mRNA is correlated with resistance to the chemotherapeutic agent 5-FU. It has been found herein that tumors expressing high levels of DPD mRNA are considered likely to be resistant to 5-FU. Conversely, those tumors expressing low amounts of DPD mRNA are likely to be sensitive to 5-FU. A patient's relative expression of tumor DPD mRNA is judged by comparing it to a predetermined threshold expression level of expression of DPD.

A predetermined threshold level of DPD mRNA expression, as defined herein, is a level of DPD expression above which it has been found that tumors are likely to be resistant to 5-FU. Expression levels below this threshold level are likely to be found in tumors sensitive to 5-FU. The range of relative expression of DPD, expressed as a ratio of DPD: an internal control gene, among tumors responding to a 5-FU based chemotherapeutic regimen responding tumors of less than about 0.6 to about 2.5, (about a 4.2-fold range). Tumors not responding to a 5-FU based chemotherapeutic regimen have relative expression of DPD : an internal control gene ratio of about 0.2 to about 16 (about an 80-fold range). Tumors generally do not respond to 5-FU treatment if there is DPD expression greater than about 2.0, preferably greater than about 2.5.

"Substantially equivalent" as used herein refers to a threshold level of DPD expression level that is about 2.0 to about 2.5.

The oligonucleotide primers of the invention enable that allow accurate assessment of DPD expression in a fixed paraffin embedded (FPE) tissue. FIG. 1. Additionally, the oligonucleotide primers of the present invention have been shown to be accurate for determining DPD expression levels in fresh or frozen tissue, i.e. they have high specificity for their target RNA. Thus, methods of the invention are not limited to use of paraffin embedded tissue. Oligonucleotide primers disclosed herein are capable of allowing accurate assessment of DPD gene expression in a fixed paraffin embedded tissue, as well as in frozen or fresh tissue. FIG. 2. This is due to the fact that the mRNA derived from FPE samples is more fragmented relative to that of fresh or frozen tissue and is therefore, more difficult to quantify. Thus, the present invention provides oligonucleotide primers that are suitable for use in assaying DPD expression levels in FPE tissue, where previously there existed no suitable assay. See FIG. 1.

Expression of DPD mRNA is correlated with clinical resistance to 5-FU-based chemotherapy. In particular, expression of high levels of DPD mRNA correlate with resistance to 5-FU-based chemotherapies. The present methods can be applied to any type of tissue. For example, for examination of resistance of tumor tissue, it is desirable to examine the tumor tissue. Preferably, it is desirable to also examine a portion of normal tissue from the patient from which the tumor is obtained. Patients whose normal tissues are resistant to 5-FU-based chemotherapeutic compounds, but whose tumors are expected to be sensitive to such compounds, may then be treated with higher amounts of the chemotherapeutic composition.

The methods in this invention are applied over a wide range of tumor types. This allows for the preparation of individual "tumor expression profiles" whereby expression levels of DPD may be determined in individual patient samples and response to various chemotherapeutics can be predicted. Most preferably, the methods of the present invention are applied to bronchalveolar, small bowel or colon tumors. For application of some embodiments of the invention to particular tumor types, it is preferable to confirm the relationship of the measurement to clinical resistance by compiling a data-set of the correlation of the particular DPD expression parameter measured and clinical resistance to 5-FU-based chemotherapy.

The methods of the present invention include the step of obtaining sample of cells from a patient's tumor. Solid or lymphoid tumors, or parts thereof are surgically resected from the patient. If it is not possible to extract RNA from the tissue sample soon after its resection, the sample may then be fixed or frozen. It will then be used to obtain RNA. RNA extracted and isolated from frozen or fresh samples of resected tissue is extracted by any of the methods typical in the art, for example, Sambrook, Fischer and Maniatis, Molecular Cloning, a laboratory manual, (2nd ed.), Cold Spring Harbor Laboratory Press, New York, (1989). Preferably, care is taken to avoid degradation of RNA during the extraction process.

Tissue obtained from the patient may fixed, preferably by formalin (formaldehyde) or gluteraldehyde treatment, for example. Biological samples fixed by alcohol immersion are also contemplated in the present invention. Fixed biological samples are often dehydrated and embedded in paraffin or other solid supports known to those of skill in the art. Such solid supports are envisioned to be removable with organic solvents, allowing for subsequent rehydration of preserved tissue. Fixed and paraffin-embedded (FPE) tissue specimen as described herein refers to storable or archival tissue samples.

RNA is extracted from the FPE cells by any of the methods as described in U.S. patent application Ser. No. 09/469,338, filed Dec. 20, 1999, which is hereby incorporated by reference in its entirety. Most preferably, RNA is extracted from tumor cells from a formalin-fixed and paraffin-embedded tissue specimen.

In an embodiment of the invention, RNA is isolated from an archival pathological sample or biopsy which is first deparaffinized. An exemplary deparaffinization method involves washing the paraffinized sample with an organic solvent, such as xylene. Deparaffinized samples can be rehydrated with an aqueous solution of a lower alcohol. Suitable lower alcohols, for example include, methanol, ethanol, propanols, and butanols. Deparaffinized samples may be rehydrated with successive washes with lower alcoholic solutions of decreasing concentration. Alternatively, the sample is simultaneously deparaffinized and rehydrated.

Once the sample is rehydrated, RNA is extracted from the rehydrated tissue. Deparaffinized samples can be homogenized using mechanical, sonic or other means of homogenization. In one embodiment, rehydrated samples are homogenized in a solution comprising a chaotropic agent, such as guanidinium thiocyanate (also sold as guanidinium isothiocyanate).

An "effective concentration of chaotropic agent" is chosen such that at an RNA is purified from a paraffin-embedded sample in an amount of greater than about 10 fold that isolated in the absence of a chaotropic agent. Chaotropic agents include: guanidinium compounds, urea, formamide, potassium iodide, potassium thiocyantate and similar compounds. The preferred chaotropic agent for the methods of the invention is a guanidinium compound, such as guanidinium isothiocyanate (also sold as guanidinium thiocyanate) and guanidinium hydrochloride. Many anionic counterions are useful, and one of skill in the art can prepare many guanidinium salts with such appropriate anions. The effective concentration of guanidinium solution used in the invention generally has a concentration in the range of about 1 to about 5M with a preferred value of about 4M. If RNA is already in solution, the guanidinium solution may be of higher concentration such that the final concentration achieved in the sample is in the range of about 1 to about 5M. The guanidinium solution also is preferably buffered to a pH of about 3 to about 6, more preferably about 4, with a suitable biochemical buffer such as Tris-Cl. The chaotropic solution may also contain reducing agents, such as dithiothreitol (DTT) and (β-mercaptoethanol (BME). The chaotropic solution may also contain RNAse inhibitors.

Homogenized samples may be heated to a temperature in the range of about 50 to about 100° C. in a chaotropic solution, which contains an effective amount of a chaotropic agent, such as a guanidinium compound. A preferred chaotropic agent is guanidinium thiocyanate.

RNA is then recovered from the solution by, for example, phenol chloroform extraction, ion exchange chromatography or size-exclusion chromatography. RNA may then be further purified using the techniques of extraction, electrophoresis, chromatography, precipitation or other suitable techniques.

The quantification of DPD mRNA from purified total mRNA from fresh, frozen or fixed is preferably carried out using reverse-transcriptase polymerase chain reaction (RT-PCR) methods common in the art, for example. Other methods of quantifying of DPD mRNA include for example, the use of molecular beacons and other labeled probes useful in multiplex PCR. Additionally, the present invention envisages the quantification of DPD mRNA via use of a PCR-free systems employing, for example fluorescent labeled probes similar to those of the Invader® Assay (Third Wave Technologies, Inc.). Most preferably, quantification of DPD cDNA and an internal control or house keeping gene (e.g. β-actin) is done using a fluorescence based real-time detection method (ABI PRISM 7700 or 7900 Sequence Detection System [TaqMan®], Applied Biosystems, Foster City, Calif.) or similar system as described by Heid et al., (Genome Res 1996;6:986–994) and Gibson et al.(Genome Res 1996;6:995–1001).

As used herein, a "house keeping" gene or "internal control" is meant to include any constitutively or globally expressed gene whose presence enables normalization of mRNA levels. Normalization is a determination of the overall constitutive level of gene transcription and a control for variations in RNA recovery. "House-keeping" genes or "internal controls" can include, but are not limited to the cyclophilin gene, β-actin gene, the transferrin receptor gene, GAPDH gene, and the like. Most preferably, the internal control gene is β-actin gene as described by Eads et al., Cancer Research 1999; 59:2302–2306.

The methods of the invention are applicable to a wide range of tissue and tumor types and so can be used for assessment of treatment in a patient and as a diagnostic or prognostic tool in a range of cancers including breast, head and neck, lung, esophageal, colorectal, and others. Preferably, the present methods are applied to prognosis of bronchoalveolar, small bowel, and colon cancer.

From the measurement of the amount of DPD mRNA that is expressed in the tumor, the skilled practitioner one can make a prognosis concerning clinical resistance of a tumor to 5-FU-based chemotherapy. 5-FU-based chemotherapy comprises administration of 5-FU, its derivatives, alone or with other chemotherapeutics or with a DPD inhibitor such as uracil, 5-ethynyluracil, bromovinyluracil, thymine, benzyloxybenzyluracil (BBU) or 5-chloro-2,4-dihydroxypyridine. Furthermore, it has been found that co-administration of a 5'-deoxy-cytidine derivative of the formula (I) with 5-FU or a derivative thereof results in significantly improved delivery of 5-FU selectively to tumor tissues as compared with the combination of 5-FU or its derivative with a DPD inhibitor 5-ethynyluracil, and shows significantly improved antitumor activity in human cancer xenograft models.

The invention being thus described, practice of the invention is illustrated by the experimental examples provided below. The skilled practitioner will realize that the materials and methods used in the illustrative examples can be modified in various ways. Such modifications are considered to fall within the scope of the present invention.

EXAMPLES

Example 1

RNA Isolation from FPE Tissue

RNA is extracted from paraffin-embedded tissue by the following general procedure.

A. Deparaffinization and Hydration of Sections:

(1) A portion of an approximately 10 $\mu$M section is placed in a 1.5 mL plastic centrifuge tube.

(2) 600 $\mu$L, of xylene are added and the mixture is shaken vigorously for about 10 minutes at room temperature (roughly 20 to 25° C.).

(3) The sample is centrifuged for about 7 minutes at room temperature at the maximum speed of the bench top centrifuge (about 10–20,000×g).

(4) Steps 2 and 3 are repeated until the majority of paraffin has been dissolved. Two or more times are normally required depending on the amount of paraffin included in the original sample portion.

(5) The xylene solution is removed by vigorously shaking with a lower alcohol, preferably with 100% ethanol (about 600 $\mu$L) for about 3 minutes.

(6) The tube is centrifuged for about 7 minutes as in step (3). The supernatant is decanted and discarded. The pellet becomes white.

(7) Steps 5 and 6 are repeated with successively more dilute ethanol solutions: first with about 95% ethanol, then with about 80% and finally with about 70% ethanol.

(8) The sample is centrifuged for 7 minutes at room temperature as in step (3). The supernatant is discarded and the pellet is allowed to dry at room temperature for about 5 minutes.

B. RNA Isolation with Phenol-Chloroform (1) 400 $\mu$L guanidine isothiocyanate solution including 0.5% sarcosine and 8 $\mu$L dithiothreitol is added.

(2) The sample is then homogenized with a tissue homogenizer (Ultra-Turrax, IKA-Works, Inc., Wilmington, N.C.) for about 2 to 3 minutes while gradually increasing the speed from low speed (speed 1) to high speed (speed 5).

(3) The sample is then heated at about 95° C. for about 5–20 minutes. It is preferable to pierce the cap of the tube containing the sample before heating with a fine gauge needle. Alternatively, the cap may be affixed with a plastic clamp or with laboratory film.

(4) The sample is then extracted with 50 $\mu$L 2M sodium acetate at pH 4.0 and 600 $\mu$L of phenol/chloroform/isoamyl alcohol (10:1.93:0.036), prepared fresh by mixing 18 mL phenol with 3.6 mL of a 1:49 isoamyl alcohol:chloroform solution. The solution is shaken vigorously for about 10 seconds then cooled on ice for about 15 minutes.

(5) The solution is centrifuged for about 7 minutes at maximum speed. The upper (aqueous) phase is transferred to a new tube.

(6) The RNA is precipitated with about 10 $\mu$L glycogen and with 400 $\mu$L isopropanol for 30 minutes at –20° C.

(7) The RNA is pelleted by centrifugation for about 7 minutes in a benchtop centrifuge at maximum speed; the supernatant is decanted and discarded; and the pellet washed with approximately 500 $\mu$L of about 70 to 75% ethanol.

(8) The sample is centrifuged again for 7 minutes at maximum speed. The supernatant is decanted and the pellet air dried. The pellet is then dissolved in an appropriate buffer for further experiments (e.g. 50 pl. 5 mM Tris chloride, pH 8.0).

Example 2 mRNA Reverse Transcription and PCR

Reverse Transcription: RNA was isolated from microdissected or non-microdissected formalin fixed paraffin embedded (FPE) tissue as illustrated in Example 1 and as previously described in U.S. application Ser. No. 09/469,338 filed Dec. 20, 1999, which is hereby incorporated by reference in its entirety. After precipitation with ethanol and centrifugation, the RNA pellet was dissolved in 50 ul of 5 mM Tris/Cl at pH 8.0. The resulting RNA was reverse transcribed with random hexamers and M-MLV from Life Technologies (CAT#28025-02.). The reverse transcription was accomplished by mixing 25 $\mu$l of the RNA solution with 25.5 $\mu$l of "reverse transcription mix" (see below). The reaction was placed in a thermocycler for 8 min at 26° C. (for binding the random hexamers to RNA), 45 min at 42° C. (for the M-MLV reverse transcription enzymatic reaction) and 5 min at 95° C. (for heat inactivation of DNAse).

"Reverse transcription mix" consisted of 10 ul 5× buffer (250 mM Tris-HCl, pH 8.3, 375 mM KCl, 15 mM MgCl2), 0.5 ul random hexamers (50 O.D. dissolved in 550 ul of 10 mM Tris-HCl pH 7.5) 5 ul 10 mM dNTPs (dATP, dGTP, dCTP and dTTP), 5 ul 0.1 M DTT, 1.25 ul BSA (3 mg/ml in 10 mM Tris-HCL, pH 7.5), 1.25 ul RNA Guard 24,800U/ml (RNAse inhibitor) (Porcine #27-0816, Amersham Pharmacia) and 2.5 ul MMLV 200U/ul (Life Tech Cat #28025-02).

Final concentrations of reaction components were: 50 mM Tris-HCl, pH 8.3, 75 mM KCl, 3 mM MgCl2, 1.0 mM dNTP, 1.0 mM DTT, 0.00375. mg/ml BSA, 0.62 U/ul RNA Guard and 10 U/ul MMLV.

PCR Quantification of mRNA Expression: Quantification of DPD cDNA and an internal control or house keeping gene (i.e. β-actin, as described in Eads et al., (Cancer Research 1999; 59:2302–2306) was done using a fluorescence based real-time detection method (ABI PRISM 7700 or 7900 Sequence Detection System [TaqMan®], Applied Biosystems, Foster City, Calif.) as described by Heid et al., (Genome Res 1996;6:986–994); Gibson et al., (Genome Res 1996;6:995–1001). In brief, this method uses a dual labelled fluorogenic oligonucleotide probe (the TaqMan® probe) that anneals specifically within the template amplicon spanning the forward and reverse primers. Laser stimulation within the capped wells containing the reaction mixture causes emission of a 3' quencher dye (TAMRA) until the probe is cleaved by the 5' to 3' nuclease activity of the DNA polymerase during PCR extension, causing release of a 5' reporter dye (6FAM). Production of an amplicon thus causes emission of a fluorescent signal that is detected by the TaqMan®'s CCD (charge-coupled device) detection camera, and the amount of signal produced at a threshold cycle within the purely exponential phase of the PCR reaction reflecting the starting copy number of the sequence of interest. TaqMan® probe for the oligonucleotide primer pair DPD1 (DPD-70F (SEQ ID NO: 3) and DPD-201R (SEQ ID NO: 4)) is DPD-108Tc (SEQ ID NO:9). TaqMan® probe for the oligonucleotide primer pair DPD2 (DPD2p-1129F (SEQ ID NO: 5) and DPD2p-1208R (SEQ ID NO: 6)) is DPD-2p-1154Tc (SEQ ID NO: 10). TaqMan® probe for the oligonucleotide primer pair DPD3A (DPD3a-51F (SEQ ID NO: 1) and DPD3a-134R (SEQ ID NO: 2)) is DPD3A-71Tc (SEQ ID NO: 11). TaqMan® probe for the oligonucleotide primer pair DPD3B (DPD3b-651F (SEQ ID NO: 7) and DPD3b-736R (SEQ ID NO: 8)) is DPD3b-685Tc (SEQ ID NO: 12).

Comparison of the starting copy number of the sequence of interest with the starting copy number of the internal control gene provided a relative gene expression level. TaqMan® analyses yield values that are expressed as ratios between two absolute measurements (gene of interest/internal control gene).

The PCR reaction contained olgionulceotide primers from the pair DPD1 (DPD-70F (SEQ ID NO: 3) and DPD-201R (SEQ ID NO: 4)); DPD2 (DPD2p-1129F (SEQ ID NO: 5) and DPD2p-1208R (SEQ ID NO: 6)); DPD3B (DPD3b-651F (SEQ ID NO: 7), $T_m$=58° C. and DPD3b-736R (SEQ ID NO: 8), $T_m$=60° C.); or oligonucleotide primer pair DPD3A (DPD3a-51F (SEQ ID NO: 1), $T_m$=59° C. and DPD3a-134R (SEQ ID NO: 2), $T_m$=59° C.). Each PCR reaction mixture consisted 0.5 μl of the reverse transcription reaction containing the cDNA as well as 600 nM each of both oligonucleotide primers from only one pair (DPD1, DPD2, DPD3B or DPD3A), 200 nM corresponding TaqMan® probe (for either DPD1, DPD2, DPD3B or DPD3A), 5 U AmpliTaq Gold Polymerase, 200 μM each dATP, dCTP, dGTP, 400 μM dTTP, 5.5 mM $MgCl_2$, and 1× Taqman Buffer A containing a reference dye, to a final volume of less than or equal to 25 μl (all reagents, Applied Biosystems, Foster City, Calif.). Cycling conditions were, 95° C. for 10 min, followed by 45 cycles at 95° C. for 15s and 60° C. for 1 min.

Example 3

DPD Expression in FPE Tumor Samples

The oligonucleotide primer pairs DPD3A (DPD3a-51F (SEQ ID NO: 1) and DPD3a-13R (SEQ ID NO: 2)) and DPD3B (DPD3b-651F (SEQ ID NO: 7) and DPD3b-736R (SEQ ID NO: 8)) allowed robust, reproducible quantitation of DPD gene expression by RT-PCR using RNA extracted from paraffin-embedded tissue. FIG. 1. Oligonucleotide primer pair DPD3A (DPD3 a-51F (SEQ ID NO: 1) and DPD3a-13R (SEQ ID NO: 2)) also significantly increased the sensitivity of DPD gene expression analysis by RT-PCR in fresh frozen tissue. FIG. 2. RT-PCR was performed using the ABI Prism 7700 Sequence Detection System (Taqman®) as described in Example 2, above.

Thirty cycles were used in the PCR reaction. Each cycle consisted of denaturing at 96° C. for 1 min, annealing at 55° C. for 1 min and extending at 72° C. for 2 min. The amplified product using oligionucleotide primer pair DPD3A (DPD3a-51F (SEQ ID NO: 1) and DPD3a-13R (SEQ ID NO: 2)) was 84 base pairs in length. The amplified product corresponded to region of DPD cDNA spanning a portion of the 5' untranslated region (UTR) and running into Exon 1. The amplified product using oligionucleotide primer pair DPD3B (DPD3b-651F (SEQ ID NO: 7) and DPD3b-736R (SEQ ID NO: 8)) is 86 base pairs in length. The amplified product corresponded to amplifies a region of DPD cDNA corresponding to Exon 6.

Oligonucleotide primer pairs DPD3A (DPD3a-51 F (SEQ ID NO: 1) and DPD3a-13R (SEQ ID NO: 2)) and DPD3B (DPD3b-651F (SEQ ID NO: 7), and DPD3b-736R (SEQ ID NO: 8)) were compared to other existing primer sets for their ability to amplify DPD mRNA derived from 10 different FPE tissue samples. Samples #1–5, and #8–10 were derived from colon, #6 from bronchoalveolar and #7 from small bowel tumor biopsies. Other oligonucleic acid primer pairs used were DPD1 (DPD-70F (SEQ ID NO: 3) and DPD-201R (SEQ ID NO: 4)) and DPD2 (DPD2p-1129F (SEQ ID NO: 5) and DPD2p-1208R (SEQ ID NO: 6)).

The oligonucleotide primer pair DPD3A (DPD3a-51F (SEQ ID NO: 1) and DPD3a-134R (SEQ ID NO: 2)) was most effective in accurately ascertaining DPD levels in various samples. Oligionucleotide primer pair DPD3B (DPD3b-651F (SEQ ID NO: 7) and DPD3b-736R (SEQ ID NO: 8)) was also effective, yet did not provide as strong a signal. Results illustrated in FIG. 1.

What is claimed is:

1. An isolated and purified oligonucleotide consisting of the sequence of SEQ ID NO: 1; wherein said isolated and purified oligonucleotide is capable of amplifying a portion of the 5' untranslated region and Exon 1 of a Dihydropyrimidine Dehydrogenase (DPD) mRNA isolated from fixed and paraffin embedded (FPE) tumor tissue when used with SEQ ID NO: 2.

2. An isolated and purified oligonucleotide consisting of the sequence of SEQ ID NO: 2; wherein said isolated and purified oligonucleotide is capable of amplifying a portion of the 5' untranslated region and Exon 1 of a Dihydropyrimidine Dehydrogenase (DPD) mRNA isolated from fixed and paraffin embedded (FPE) tumor tissue when used with SEQ ID NO: 1.

3. An isolated and purified oligonucleotide consisting of the sequence of SEQ ID NO: 7; wherein said isolated and purified oligonucleotide is capable of amplifying a portion of Exon 6 of a Dihydropyrimidine Dehydrogenase (DPD) mRNA isolated from fixed and paraffin embedded (FPE) tumor tissue when used with SEQ ID NO: 8.

4. An isolated and purified oligonucleotide consisting of the sequence of SEQ ID NO: 8; wherein said isolated and purified oligonucleotide is capable of amplifying a portion of Exon 6 of a Dihydropyrimidine Dehydrogenase (DPD) mRNA isolated from fixed and paraffin embedded (FPE) tumor tissue when used with SEQ ID NO: 7.

5. A kit for detecting expression of a Dihydropyrimidine Dehydrogenase (DPD) gene in a tissue comprising at least two oligonucleotide primers, said two oligonucleotide primers consisting of SEQ ID NO: 1; capable of amplifying a portion of a Dihydropyrimidine Dehydrogenase (DPD) mRNA isolated from fixed and paraffin embedded (FPE) tumor tissue when used with SEQ ID NO:2; and SEQ ID NO: 2; capable of amplifying a portion of a Dihydropyrimidine Dehydrogenase (DPD) mRNA isolated from fixed and paraffin embedded (FPE) tumor tissue when used with SEQ ID NO: 1.

6. A kit for detecting expression of a Dihydropyrimidine Dehydrogenase (DPD) gene in a tissue comprising at least two oligonucleotide primers, said two oligonucleotide primers consisting of SEQ ID NO:7 capable of amplifying portion of a Dihydropyrimidine Dehydrogenase (DPD) mRNA isolated from fixed and paraffin embedded (FPE) tumor tissue when used with SEQ ID NO: 8; and SEQ ID NO: 8; capable of amplifying a portion of a Dihydropyrimidine Dehydrogenase (DPD) mRNA isolated from fixed and paraffin embedded (FPE) tumor tissue when used with SEQ ID NO: 7.

* * * * *

UNITED STATES PATENT AND TRADEMARK OFFICE
CERTIFICATE OF CORRECTION

PATENT NO.    : 6,956,111 B2
DATED         : October 18, 2005
INVENTOR(S)   : Kathleen D. Danenberg It is certified that error appears in the above-identified patent and that said Letters Patent is hereby corrected as shown below:

Column 3,
Line 28, change "parafin" to -- paraffin --;
Line 67, change "oligionucleotide" to -- oligonucleotide --;

Column 4,
Lines 20 and 55, change "oligionucleotide" to -- oligonucleotide --;

Column 5,
Line 32, change "at least least" to -- at least --;
Line 41, change "temperture" to -- temperature --;
Line 47, change "holmologous" to -- homologous --;
Line 49, change "temperatre" to -- temperature --;
Line 59, change "be varied" to -- are varied --;

Column 6,
Line 4, change "oligionucleotide" to -- oligonucleotide --;
Line 43, change "enable that allow" to -- provide for or allow --;

Column 7,
Line 13, change "bronchalveolar" to -- bronchoalveolar --;
Line 34, change "gluteraldehyde" to -- glutaraldehyde --;

Column 8,
Line 8, change "iodiode" to -- iodide --; and

Column 11,
Line 41, change "oligionucleotide" to -- oligonucleotide --.

Signed and Sealed this

Twenty-first Day of February, 2006

JON W. DUDAS
*Director of the United States Patent and Trademark Office*

SEQUENCE LISTING

<160> NUMBER OF SEQ ID NOS: 12

<210> SEQ ID NO 1
<211> LENGTH: 19
<212> TYPE: DNA
<213> ORGANISM: Artificial Sequence
<220> FEATURE:
<223> OTHER INFORMATION: Oligonucleotide Primer

<400> SEQUENCE: 1
aggacgcaag gagggtttg                                              19

<210> SEQ ID NO 2
<211> LENGTH: 20
<212> TYPE: DNA
<213> ORGANISM: Artificial Sequence
<220> FEATURE:
<223> OTHER INFORMATION: Oligonucleotide Primer

<400> SEQUENCE: 2
gtccgccgag tccttactga                                             20

<210> SEQ ID NO 3
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 3
tcactggcag actcgagact gt                                          22

<210> SEQ ID NO 4
<211> LENGTH: 18
<212> TYPE: DNA
<213> ORGANISM: Artificial Sequence
<220> FEATURE:
<223> OTHER INFORMATION: Oligonucleotide Primer

<400> SEQUENCE: 4
tggccgaagt ggaacaca                                               18

<210> SEQ ID NO 5
<211> LENGTH: 22
<212> TYPE: DNA
<213> ORGANISM: Artificial Sequence
<220> FEATURE:
<223> OTHER INFORMATION: Oligonucleotide Primer

<400> SEQUENCE: 5
ctgcctttga ctgtgcaaca tc                                          22

<210> SEQ ID NO 6
<211> LENGTH: 27
<212> TYPE: DNA
<213> ORGANISM: Artificial Sequence
<220> FEATURE:
<223> OTHER INFORMATION: Oligonucleotide Primer

<400> SEQUENCE: 6
attaacaaag cctttctga agacgat                                      27

<210> SEQ ID NO 7
<211> LENGTH: 23
<212> TYPE: DNA
<213> ORGANISM: Artificial Sequence
<220> FEATURE:
<223> OTHER INFORMATION: Oligonucleotide Primer

<400> SEQUENCE: 7
gaagcctatt ctgcaaagat tgc                                         23

<210> SEQ ID NO 8
<211> LENGTH: 21
<212> TYPE: DNA

```
<213> ORGANISM: Artificial Sequence
<220> FEATURE:
<223> OTHER INFORMATION: Oligonucleotide Primer

<400> SEQUENCE: 8
gagtacccca atcgagccaa a                                              21

<210> SEQ ID NO 9
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 9
ccgccgagtc cttactgagc acagg                                          25

<210> SEQ ID NO 10
<211> LENGTH: 25
<212> TYPE: DNA
<213> ORGANISM: Artificial Sequence
<220> FEATURE:
<223> OTHER INFORMATION: Oligonucleotide Primer

<400> SEQUENCE: 10
cacacggcga gctccacaac gtaga                                          25

<210> SEQ ID NO 11
<211> LENGTH: 29
<212> TYPE: DNA
<213> ORGANISM: Artificial Sequence
<220> FEATURE:
<223> OTHER INFORMATION: Oligonucleotide Primer

<400> SEQUENCE: 11
cagtgcctac agtctcgagt ctgccagtg                                      29

<210> SEQ ID NO 12
<211> LENGTH: 31
<212> TYPE: DNA
<213> ORGANISM: Artificial Sequence
<220> FEATURE:
<223> OTHER INFORMATION: Oligonucleotide Primer

<400> SEQUENCE: 12
aaggaagcac aacttatact tgcaggccca g                                   31
```